United States Patent
Vijaysri Nair et al.

(10) Patent No.: US 9,976,175 B2
(45) Date of Patent: May 22, 2018

(54) CALIBRATION METHOD, APPARATUS AND COMPUTER PROGRAM PRODUCT

(71) Applicant: GEN-PROBE INCORPORATED, San Diego, CA (US)

(72) Inventors: Sangeetha Vijaysri Nair, San Diego, CA (US); Xianqun Wang, San Marcos, CA (US); Susan K. Yamagata, Encinitas, CA (US)

(73) Assignee: Gen-Probe Incorporated, San Diego, CA (US)

( * ) Notice: Subject to any disclaimer, the term of this patent is extended or adjusted under 35 U.S.C. 154(b) by 545 days.

(21) Appl. No.: 14/211,565

(22) Filed: Mar. 14, 2014

(65) Prior Publication Data

US 2014/0272991 A1    Sep. 18, 2014

Related U.S. Application Data

(60) Provisional application No. 61/792,409, filed on Mar. 15, 2013.

(51) Int. Cl.
*G06F 19/24* (2011.01)
*C12Q 1/68* (2006.01)

(52) U.S. Cl.
CPC ......... *C12Q 1/6844* (2013.01); *C12Q 1/6851* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 6,066,458 | A | 5/2000 | Haaland et al. |
| 6,503,720 | B2 | 1/2003 | Wittwer et al. |
| 6,713,297 | B2 | 3/2004 | McMillan et al. |
| 6,783,934 | B1 | 8/2004 | McMillan et al. |
| 7,630,837 | B2 | 12/2009 | Eyre et al. |
| 7,739,054 | B2 | 6/2010 | Carrick et al. |
| 7,897,337 | B2 | 3/2011 | Macioszek et al. |
| 7,930,106 | B2 | 4/2011 | Carrick |
| 8,615,368 | B2 | 12/2013 | Light, II et al. |
| 2011/0147610 | A1 | 6/2011 | Macioszek et al. |

FOREIGN PATENT DOCUMENTS

| | | |
|---|---|---|
| DE | 196 14 852 A1 | 10/1997 |
| EP | 1 138 784 B1 | 10/2008 |
| WO | 2008067567 A2 | 6/2008 |
| WO | 2014018885 A2 | 1/2014 |

OTHER PUBLICATIONS

Gill et al. Nucleic Acid Isothermal Amplification Technologies—A Review Nucleosides, Nucleotides, and Nucleic Acids vol. 27, pp. 224-243 (2008).*
Nordstrom et al. Development of a Multiplex Real-Time PCR Assay with an Internal Amplification Control for the Detection of Total and Pathogenic Vibrio parahaemolyticus Bacteria in Oysters Applied and Environmental Microbiology vol. 73, pp. 5840-5847 (2007).*
Hymas W., et al. "Use of lyophilized standards for the calibration of a newly developed real time PCR assay for human herpes type six (HHV6) variants A and B", Journal of Virological Methods, Sep. 1, 2005 (Sep. 1, 2005), pp. 143-150, vol. 128. No. 1-2, Elsevier BV. N L.
International Search Report, International Application No. PCT/US2014/027628, dated Jun. 11, 2014.
Written Opinion of the International Searching Authority, International Application No. PCT/US2014/027628, dated Jun. 11, 2014.
International Preliminary Report on Patentability, International Application No. PCT/US2014/027628, dated Sep. 15, 2015.
Gill et al., "Nucleic Acid Isothermal Amplification Technologies—a Review," Nucleosides, Nucleotides and Nucleic Acids, 27:224-243, 2008.
Nordstrom et al., "Development of a Multiplex Real-Time PCR Assay with an Internal Amplification Control for the Detection of Total and Pathogenic Vibrio parahaemolyticus Bacteria in Oysters," Applied and Environmental Microbiology, 2007, p. 5840-5847.
SIPO Office Action and Search Report, Chinese Patent Application No. 201480012147.0, dated Jun. 30, 2017.
JPO Office Action, Japanese Patent Application No. 2016-502497, dated Jan. 11, 2018.

* cited by examiner

*Primary Examiner* — John S Brusca
(74) *Attorney, Agent, or Firm* — McNeill Baur PLLC

(57) ABSTRACT

Method and system for quantifying target nucleic acids using real-time amplification and internal calibration adjustment. The approach employs a single fixed data point in combination with a single adjustment calibrator amplified on the instrument that is to be calibrated for approximating a complete calibration curve.

31 Claims, No Drawings

CALIBRATION METHOD, APPARATUS AND COMPUTER PROGRAM PRODUCT

CROSS-REFERENCE TO RELATED APPLICATION

This application claims the benefit of U.S. Provisional Application No. 61/792,409, filed Mar. 15, 2013, the contents of which application are hereby incorporated by reference herein in its entirety.

FIELD

The present disclosure relates to the field of biotechnology. More specifically, the disclosure relates to calibration methods and systems for quantifying polynucleotides using results from real-time amplification procedures.

BACKGROUND

Methods involving the kinetic analysis of in vitro nucleic acid amplification are now routinely used for quantifying analyte nucleic acids. In these procedures, sometimes referred to as "real-time" amplification procedures, the amount of amplicon present in a nucleic acid amplification reaction mixture is monitored as a function of time over the course of the amplification procedure. Fully automated real-time nucleic acid assays require machine executable algorithms capable of analyzing the time-dependent data acquired during the reaction. In this regard, there is a requirement for data processing algorithms that accurately output an amount or concentration of a nucleic acid that would give rise to an observed amplification result.

Difficulties associated with quantifying the absolute amount of a specific nucleic acid target have been appreciated in the patent literature. These difficulties have been attributed to the exponential nature of the amplification process, and the fact that small differences in any of the variables that control reaction rates, including the length and nucleotide sequence of the primer pairs, can lead to dramatic differences in amplicon yield. Wang et al., in U.S. Pat. No. 5,219,727 described the use of an internal standard that amplified using the same primers that amplified the analyte polynucleotide, and addressed the fact that use of an unrelated cDNA as a standard necessitated a second set of oligonucleotide primers unrelated to the specific target nucleic acid being quantified. According to Wang et al., analyses which use two sets of unrelated primers can only provide a relative comparison of two independent amplification reactions rather than an absolute measure of a target nucleic acid concentration. Others have followed this teaching and employed internal standards that resemble the target of interest by having similar sequences, and by amplifying with a common pair of primers (see published U.S. patent application Ser. No. 10/230,489). Still others have described quantitative methods that rely on determining the efficiency of amplification (see published European Patent Application EP 1138784). Methods involving determination of amplification ratios for control and target sequences also have been described (see U.S. Pat. No. 6,066,458).

The most common methods for performing internal calibration adjustment of real-time nucleic acid amplification results include "within-run" calibration adjustment, and adjustment of a "stored" calibration curve. The first of these methods, illustrated by McMillan et al., in U.S. Pat. No. 6,713,297, requires two or more calibration standards that are conventionally amplified in parallel with analyte nucleic acids in replicates each time a calibration plot is prepared. Unfortunately, this requirement each time an instrument is re-calibrated consumes limited reagents that are generally purchased in kit form, and that may be costly. The second method, illustrated by Carrick in U.S. Pat. No. 7,930,106, advantageously avoids the need to run multiple calibrators each time an instrument is re-calibrated, but still requires preparation of a full calibration plot at some point (e.g., either by a kit manufacturer or end-user). Experience with this technique has shown good ability to reproduce quantitative results using a single calibration standard when the target being quantified is present at high, or very high levels. For example, back-testing confirmed that adjustment of a stored curve using a single adjustment calibrator having $10^7$ target copies advantageously reproduced the full local curve nearly identically in the range of from $10^4$ to $10^8$ target copies. In this case, the adjusted curve deviated from the local curve by no more than 0.6 log copies at an input amount of $10^2$ target copies. Using a single adjustment calibrator having $10^2$ target copies, in contrast, resulted in an adjusted curve deviating by 0.4 log copies at an input target level of $10^3$ target copies, and deviating by 1.6 log copies at an input target level of $10^6$ target copies. Thus, there was a clear benefit to adjusting the stored curve using calibration standards having high target amounts.

Even in view of these useful approaches, there remains a need for automated solutions that permit highly accurate quantitation of nucleic acids using in vitro amplification techniques, where internal calibration adjustment can be executed in a simplified manner. Moreover, it would be desirable to be able to use a single calibration standard that comprises a low concentration of the analyte polynucleotide standard to achieve accurate quantitation across the full dynamic range of target amounts or concentrations to be measured. The present disclosure addresses these issues.

SUMMARY

A first aspect of the disclosure regards a method of establishing an adjusted calibration curve for a quantitative assay performed using a local instrument that amplifies nucleic acid and monitors amplicon synthesis as amplification is occurring. The method includes the step (a) of obtaining a pair of coordinates for a fixed-point on a calibration curve specific for the quantitative assay, wherein the pair of coordinates specify an amount of an analyte polynucleotide and a normalized indicia of amplification value. There also is the step (b) of obtaining an adjustment calibrator that includes a fixed amount of an internal calibrator and a known amount of the analyte polynucleotide. There also is the step (c) of co-amplifying the analyte polynucleotide and the internal calibrator of the adjustment calibrator using the local instrument. There also is the step (d) of determining indicia of amplification for each of the analyte polynucleotide and the internal calibrator that co-amplified in step (c). There also is the step (e) of normalizing the indicia of amplification determined for the analyte polynucleotide to the indicia of amplification determined for the internal calibrator. There also is the step (f) of establishing the adjusted calibration curve by preparing a calibration plot that includes a first point and a second point, wherein the first point includes coordinates for the known amount of the analyte polynucleotide of the adjustment calibrator and the normalized indicia of amplification for the analyte polynucleotide determined in step (d), and wherein the second point includes the pair of coordinates, obtained in step (a), for the fixed-point. In a preferred embodiment, the amount of the analyte polynucleotide specified by the pair of coordinates obtained in step (a) is determined using a first real-time amplification and monitoring instrument other than the local instrument, and is not determined using results from any amplification reaction performed with the local instrument. More preferably, the method further includes the step of co-amplifying with the first real-time instrument the analyte polynucleotide and the internal calibrator contained in each of a plurality of calibration standards, wherein each of the plurality of calibration standards includes a different starting concentration of the analyte polynucleotide of the adjustment calibrator, and wherein the concentrations of the internal calibrator in each of the plurality of calibration standards and in the adjustment calibrator are substantially identical. Alternatively, the calibration curve of step (a) and the adjusted calibration curve established in step (f) may both be linear calibration curves described by linear equations. According to a different preferred embodiment, step (a) and step (b) collectively involve obtaining (e.g., purchasing) a kit that includes the adjustment calibrator and a tangible embodiment of the pair of coordinates for the fixed-point. When this is the case, the tangible embodiment may include a machine-readable barcode. According to yet another preferred embodiment, before step (a) there is the step of preparing the calibration curve specific for the quantitative assay by fitting an equation to a collection of results obtained using a plurality of instruments, other than the local instrument, that amplify nucleic acid and monitor amplicon synthesis as amplification is occurring, wherein the collection of results does not include results obtained using the local instrument. According to yet another preferred embodiment, step (f) involves establishing the adjusted calibration curve by preparing, with a processor in communication with the local instrument, the calibration plot that comprises the first point and the second point. For example, the processor in communication with the local instrument may be an integral component of the local instrument. According to yet another preferred embodiment, the pair of coordinates obtained in step (a) specifies the amount of the analyte polynucleotide when the normalized indicia of amplification value of the calibration curve is zero. In accordance with certain embodiments wherein the amount of the analyte polynucleotide specified by the pair of coordinates obtained in step (a) is determined using a first real-time amplification and monitoring instrument other than the local instrument, and is not determined using results from any amplification reaction performed with the local instrument, the pair of coordinates obtained in step (a) specifies the amount of the analyte polynucleotide when the normalized indicia of amplification value of the calibration curve is zero. In accordance with different preferred embodiments wherein before step (a) there is the step of preparing the calibration curve specific for the quantitative assay by fitting an equation to a collection of results obtained using a plurality of instruments, other than the local instrument, that amplify nucleic acid and monitor amplicon synthesis as amplification is occurring, and wherein the collection of results does not include results obtained using the local instrument, the pair of coordinates obtained in step (a) specifies the amount of the analyte polynucleotide when the normalized indicia of amplification value of the calibration curve is zero.

Another aspect of the disclosure regards a computer program product for quantifying an analyte polynucleotide that may be present in a test sample using a nucleic acid amplification assay that involves co-amplification, with a local instrument that amplifies nucleic acids and monitors amplicon synthesis as a function of time, of the analyte polynucleotide and a fixed amount of an internal calibrator. The computer program product includes a tangible embodiment of software instructions for performing a series of steps. These steps include the step (a) of receiving a pair of coordinates for a fixed-point on a calibration curve specific for the nucleic acid amplification assay to be used for quantifying the analyte polynucleotide, wherein the pair of coordinates specify an amount of the analyte polynucleotide and a normalized indicia of amplification value. There also is the step (b) of obtaining a value for indicia of amplification for a known amount of the analyte polynucleotide normalized to indicia of amplification for the fixed amount of the internal calibrator contained in an adjustment calibrator and that co-amplified in a first amplification reaction performed with the local instrument. There also is the step (c) of preparing an adjusted calibration curve that includes a first point and a second point, wherein the first point includes coordinates for the known amount of the analyte polynucleotide of the adjustment calibrator and the value obtained in step (b), and wherein the second point includes the pair of coordinates, received in step (a), for the fixed-point. There also is the step (d) of obtaining a value for indicia of amplification for an unknown amount of the analyte polynucleotide in the test sample normalized to indicia of amplification for the fixed amount of the internal calibrator that co-amplified therewith in a second amplification reaction performed with the local instrument. There also is the step (e) of comparing the value obtained in step (d) with the adjusted calibration curve to yield a quantitative result for the unknown amount of the analyte polynucleotide present in the test sample. There also is the step (f) of outputting a tangible record of the quantitative result from step (e). In a preferred embodiment, the pair of coordinates received in step (a) specifies the amount of the analyte polynucleotide when the calibration curve is projected to a normalized indicia of amplification value of zero. In a different embodiment, the tangible embodiment of software instructions includes software instructions stored on a medium that may be any of: an optical disk, a magnetic storage medium, a flash drive, a computer hard drive, and a network drive accessible by at least one computer. In a different embodiment, step (b) and step (d) each involve obtaining by mathematically calculating. In a different embodiment, steps (b) and (d) involve obtaining by receiving numerical inputs for the respective values. In a different embodiment, the adjusted calibration curve prepared in step (c) is defined by a linear equation. In a different embodiment, the tangible record of step (e) is printed on paper. In a different embodiment, the nucleic acid amplification assay is an isothermal nucleic acid amplification assay.

Another aspect of the disclosure relates to an apparatus for determining the starting quantity of a target nucleic acid sequence in a test sample. The apparatus includes (a) at least one detection mechanism that measures: (i) signals indicative of the respective quantities of the target nucleic acid sequence and of a first internal calibrator being amplified in a first nucleic acid amplification reaction, wherein the first internal calibrator includes a second nucleic acid sequence different from the target nucleic acid sequence; (ii) signals indicative of the respective quantities of a known amount of an analyte polynucleotide and a second internal calibrator being amplified in a second nucleic acid amplification reaction, wherein the analyte polynucleotide and the second internal calibrator are both components of an adjustment calibrator, wherein the second internal calibrator includes the second nucleic acid sequence, and wherein the starting quantity of the second nucleic acid sequence is substantially equal in the first and second nucleic acid amplification reactions. The invented apparatus further includes (b) at least one processor in communication with the detection mechanism, wherein the processor is programmed with a pair of coordinates for a fixed-point specifying an analyte polynucleotide amount and a normalized indicia of amplification value, and wherein the processor further is programmed to perform the steps of: (i) determining from the measured signals respective values for indicia of amplification for the known amount of the analyte polynucleotide, each of the first and second internal calibrators, and the target nucleic acid sequence; (ii) normalizing the indicia of amplification value determined for the target nucleic acid sequence to the indicia of amplification value determined for the first internal calibrator; (iii) normalizing the indicia of amplification value determined for the known amount of the analyte polynucleotide to the indicia of amplification value determined for the second internal calibrator; (iv) establishing a calibration curve from the fixed-point, the known amount of the analyte polynucleotide and the normalized indicia of amplification for the known amount of the analyte polynucleotide; and (v) determining the starting quantity of the target nucleic acid sequence in the test sample using the calibration curve and the normalized indicia of amplification for the target nucleic acid sequence. In a preferred embodiment, the pair of coordinates for the fixed-point are determined using results from a plurality of nucleic acid amplification reactions performed using only an apparatus other than the apparatus that performed the first and second nucleic acid amplification reactions. More preferably, one member of the pair of coordinates specifies a normalized indicia of amplification value of zero. Alternatively, the apparatus may further include a temperature-controlled incubator in which the first and second nucleic acid amplification reactions take place. In a particular instance, the temperature-controlled incubator maintains a substantially constant temperature, and the first and second nucleic acid amplification reactions are isothermal nucleic acid amplification reactions. In accordance with a different preferred embodiment, the calibration curve in step (iv) is defined by a linear equation. In accordance with yet a different preferred embodiment, the at least one detection mechanism includes a fluorometer that measures fluorescent signals.

Another aspect of the disclosure relates to a method of establishing an adjusted calibration curve for a quantitative assay performed using a local instrument that amplifies nucleic acid and monitors amplicon synthesis as amplification is occurring. The invented method includes the step (a) of obtaining a pair of coordinates for a fixed-point on a calibration curve specific for the quantitative assay, wherein the pair of coordinates specify an amount of an analyte polynucleotide and an indicia of amplification value. There also is the step (b) of obtaining an analyte polynucleotide standard that includes a known amount of the analyte polynucleotide. There also is the step (c) of amplifying the analyte polynucleotide of the analyte polynucleotide standard in a nucleic acid amplification reaction using the local instrument. There also is the step (d) of determining indicia of amplification for the analyte polynucleotide that amplified in step (c). There also is the step (e) of establishing the adjusted calibration curve by preparing a calibration plot that includes a first point and a second point, wherein the first point includes coordinates for the known amount of the analyte polynucleotide of the analyte polynucleotide standard and indicia of amplification determined in step (d), and wherein the second point includes the pair of coordinates, obtained in step (a), for the fixed-point. In a preferred embodiment, before step (a) there is the step of preparing the calibration curve specific for the quantitative assay by fitting an equation to a collection of results obtained using a plurality of instruments, other than the local instrument, that amplify nucleic acid and monitor amplicon synthesis as amplification is occurring, and wherein the collection of results does not include results obtained using the local instrument. In accordance with a different preferred embodiment, step (e) includes using a processor in communication with the local instrument to prepare the calibration plot.

DETAILED DESCRIPTION

Introduction

Disclosed herein is an internal calibration approach that employs results determined on an end-user's instrument in combination with a stored point (e.g., a "fixed-point") on a calibration plot. Optionally, the fixed-point can be determined on the end-user's instrument and then stored for later use on that same instrument. Alternatively, the fixed-point can be determined using one or more instruments (e.g., at a kit manufacturer's location), and then provided for use on the end-user's instrument. The disclosed approach advantageously facilitates production of a full calibration curve for nucleic acid quantitation using as few as a single nucleic acid calibration standard. Too, the approach simplifies workflow and is more cost-effective than production of a complete calibration curve using a full set of calibrators each time a re-calibration procedure is needed. Still further, the approach provides outstanding quantitation over an extended dynamic range, and accommodates the use of aged or partially degraded reagents.

Particularly useful systems and methods will be capable of reproducing a complete calibration curve using a minimal number of calibration standards amplified on an end-user's instrument that is to be calibrated. Indeed, by the approach detailed herein, outstanding results have been achieved using only a single calibration standard to recreate a complete calibration curve. This can involve first establishing a calibration reference curve using a plurality of calibration standards, each having a different amount of analyte polynucleotide standard and the same constant amount of internal calibrator (i.e., "IC"). Next, an extrapolated point on the reference curve can be identified for use as a fixed-point. Results from an amplification reaction performed using a calibration standard (e.g., a single calibration standard) on an end-user's instrument can then be used to determine a target/IC ratio value (i.e., the ratio of respective indicia of amplification), thereby establishing a "local" (e.g., produced by an end-user) data point. The local data point and the fixed-point can be used in combination to produce an "adjusted calibration curve," such as a linear calibration curve. Finally, there is a step for quantifying target amounts present in test samples on the end-user's instrument using the adjusted calibration curve. Preferably, this involves comparing a ratio value calculated using measured indicia of amplification for target and IC obtained by amplification of a test sample with the adjusted calibration curve.

According to a first embodiment, a master calibration curve is prepared using results (e.g., normalized threshold or other indicia of amplification values for amplified target and IC) from two or more amplification reactions performed using different calibration standards on a first instrument that amplifies nucleic acids and monitors amplicon production as a function of time or cycle number. Threshold $C_T$ values, or other indicia of amplification indicative of a particular level of reaction progress for amplification of target nucleic acid in the calibration standards are normalized to corresponding values for IC determined for the same reactions, for example by division to result in ratios. The ratio value calculated for each of the two or more calibration reactions is then plotted (e.g., using an electronic spreadsheet) as a function of the starting amount of target input into the reaction. In some preferred instances, a linear calibration plot is established.

A calibration or re-calibration procedure can be preformed using as few as one calibration standard having a known starting copy level of target nucleic acid, and the same constant amount of IC as employed in the reactions used to establish the calibration curve that can be used to establish the fixed-point. Determining and normalizing threshold values for target and IC in the real-time amplification reaction yields one point that can be used in combination with the fixed-point to generate the full calibration plot.

As indicated above, there are different ways in which the fixed-point can be used in combination with a second point to generate the calibration plot. In a first instance, the fixed-point and ratio value determined for the calibration standard are both generated on the same instrument (e.g., "first" instrument). In a second case, the fixed-point and ratio value determined for the calibration standard are generated on different instruments (e.g., first and second instruments). In both cases, the technique advantageously corrects calibration plots to account for aged reagents, including reagents that have been cycled on and off a particular instrument several times. As well, the technique does not depend on determination of amplification efficiencies. Still further, it is not required that the copy level or amount of IC included in each reaction is known. However, the IC copy level or amount in each reaction should be the same.

Definitions

The following terms have the following meanings for the purpose of this disclosure, unless expressly stated to the contrary herein.

As used herein, "polynucleotide" means either RNA, DNA, or a chimeric molecule containing both RNA and DNA. The term also embraces molecules containing nucleotide analogs of RNA or DNA.

By "analyte polynucleotide" or "analyte nucleic acid" is meant a polynucleotide of interest that is to be quantified. Generally speaking, analyte nucleic acids will be found in test samples. The genome of a particular virus would exemplify an analyte polynucleotide.

As used herein, a "test sample" is any sample to be investigated for the presence of a particular polynucleotide sequence. Test samples include any tissue or polynucleotide-containing material obtained from a human, animal, environmental, or laboratory-derived or synthetic sample. Blood and urine are preferred examples of test samples.

By "analyte polynucleotide standard" is meant a composition comprising a known quantity of an analyte polynucleotide, or fragment thereof. For example, an HIV-1 analyte polynucleotide standard may contain a known number of copies of an HIV-1 genome, HIV-1 transcript, or in vitro synthesized transcript representing a portion of the viral genome.

By "calibration standard" is meant a composition that includes a known or predetermined amount of analyte polynucleotide standard in combination with a known constant amount of an internal calibrator polynucleotide. Two different calibration standards can contain different amounts of analyte polynucleotide or a fragment thereof, but will contain the same amount of internal calibrator nucleic acid. The analyte polynucleotide of the analyte polynucleotide standard, and the internal calibrator nucleic acid will be distinguishable from each other, for example by having nucleotide base sequences that are different.

"Adjustment calibrators" are calibration standards used for conducting amplification reactions on a local instrument, where results obtained from those amplification reactions provide data for creating a calibration plot. For example, amplification of an adjustment calibrator may provide a data point that may be used in combination with a fixed-point to create a full calibration plot.

An "amplicon" is a polynucleotide product of an amplification reaction, wherein a target nucleic acid sequence served as the template for synthesis of polynucleotide copies or amplification products.

By "amplification" or "nucleic acid amplification" or "in vitro nucleic acid amplification" and the like is meant any known procedure for obtaining multiple copies, allowing for RNA and DNA equivalents, of a target nucleic acid sequence or its complement or fragments thereof. Amplification of "fragments thereof" refers to production of an amplified nucleic acid containing less than the complete target region nucleic acid sequence or its complement. Such fragments may be produced by amplifying a portion of the target nucleic acid, for example, by using an amplification oligonucleotide that hybridizes to, and initiates polymerization from, an internal position of the target nucleic acid.

As used herein, the terms "coamplify" and "coamplifying" and variants thereof refer to a process wherein different target nucleic acid sequences are amplified in a single (i.e., the same) amplification reaction. For example, an analyte polynucleotide and an unrelated internal calibrator nucleic acid are "coamplified" when both nucleic acids are amplified in reactions taking place in a single tube, and when both amplification reactions share at least one reagent (e.g., deoxyribonucleotide triphosphates, enzyme, primer(s), etc.) in common.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target" or "target nucleic acid" is meant a nucleic acid containing a sequence that is to be amplified, detected and quantified. A target nucleic acid sequence that is to be amplified preferably will be positioned between two oppositely disposed oligonucleotides, and will include the portion of the target nucleic acid that is complementary to each of the oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription-associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target nucleic acid. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. patent application having Ser. No. 11/213,519 are particularly embraced by the definition and are highly preferred for use in connection with the method disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present disclosure fall in a size range of about 10 to about 100 residues. Oligonucleotides may be purified from naturally occurring sources, but preferably are synthesized using any of a variety of well known enzymatic or chemical methods.

By "amplification oligonucleotide" or "amplification oligomer" is meant an oligomer that hybridizes to a target nucleic acid, or its complement, and participates in a nucleic acid amplification reaction. Examples of amplification oligomers include primers that contain a 3' end that is extended as part of the amplification process, but also include oligomers that are not extended by a polymerase (e.g., a 3' blocked oligomer) but may participate in, or facilitate efficient amplification from a primer. Preferred size ranges for amplification oligomers include those that are about 10 to about 80 nucleotides long, or 10 to about 60 nucleotides long and contain at least about 10 contiguous bases, and more preferably at least 12 contiguous bases that are complementary to a region of the target nucleic acid sequence (or a complementary strand thereof). The contiguous bases are preferably at least about 80%, more preferably at least about 90%, and most preferably about 100% complementary to the target sequence to which amplification oligomer binds. An amplification oligomer may optionally include modified nucleotides or analogs, or additional nucleotides that participate in an amplification reaction but are not complementary to or contained in the target nucleic acid. An amplification oligomer that is 3' blocked but capable of hybridizing to a target nucleic acid and providing an upstream promoter sequence that serves to initiate transcription is referred to as a "promoter provider" oligomer.

A "primer" is an amplification oligomer that hybridizes to a template nucleic acid and has a 3' OH end that can be extended by a DNA polymerase. The 5' region of the primer may be non-complementary to the target nucleic acid (e.g., a promoter sequence), resulting in an oligomer referred to as a "promoter-primer." Those skilled in the art will appreciate that any oligomer that can function as a primer can be modified to include a 5' promoter sequence, and thus could function as a promoter-primer. Similarly, any promoter-primer can be modified by removal of, or synthesis without, a promoter sequence and still function as a primer.

As used herein, a "set" of amplification oligonucleotides refers to a collection of two or more amplification oligonucleotides that cooperatively participate in an in vitro nucleic acid amplification reaction to synthesize amplicons.

As used herein, a "probe" is an oligonucleotide that hybridizes specifically to a target sequence in a nucleic acid, preferably in an amplified nucleic acid, under conditions that promote hybridization, to form a detectable hybrid.

As used herein, "time-dependent" monitoring of nucleic acid amplification, or monitoring of nucleic acid amplification in "real-time" refers to a process wherein the amount of amplicon present in a nucleic acid amplification reaction is measured as a function of reaction time or cycle number, and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement (y-axis). Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation generally is substantially lower than the rate of amplicon production in the log-linear phase, and may even approach zero.

As used herein, the phrase "indicia of amplification" refers to features of real-time run curves which indicate a predetermined level of progress in nucleic acid amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

As used herein, the phrase "threshold-based indicia of amplification" refers to indicia of amplification that measure the time or cycle number when a growth curve signal crosses an arbitrary value or threshold. TTime determinations are examples of threshold-based indicia of amplification, while TArc and OTArc determinations are examples of non-threshold-based indicia of amplification.

As used herein, the phrase "time-dependent" indicia of amplification refers generally to indicia of amplification (e.g., a reaction progress parameter) that are measured in time units (e.g., minutes). Time-dependent indicia of amplification are commonly used for monitoring progress in isothermal nucleic acid amplification reactions that are not characterized by distinct "cycles." All of TTime, TArc and OTArc are examples of time-dependent indicia of amplification.

As used herein, an "internal calibrator" (sometimes "IC" herein) is a polynucleotide that can be amplified in an in vitro nucleic acid amplification reaction, and that is distinguishable from an analyte polynucleotide that coamplified in the same reaction. "Internal" means that the calibrator polynucleotide is amplified, detected and quantified within the same reaction mixture as the analyte polynucleotide, or fragment thereof. Generally speaking, the amount or concentration of the internal calibrator will be constant in different reactions used for preparing calibration curves, and for quantifying the analyte polynucleotide. Preferably, the constant amount or concentration of internal calibrator will be a known amount of internal calibrator, or a known concentration of internal calibrator. In certain preferred embodiments, the internal calibrator and the analyte polynucleotide are coamplified in an in vitro nucleic acid amplification reaction using one or more different amplification oligomers or primers. For example, the analyte and internal calibrator polynucleotides employed in the working Examples detailed below were amplified using amplification oligonucleotides that were not shared. In other preferred embodiments, the internal calibrator and the analyte polynucleotide are coamplified in an in vitro nucleic acid amplification reaction using one or more identical amplification oligomers or primers.

As used herein, the phrase "as a function of" describes the relationship between a dependent variable (i.e., a variable that depends on one or more other variables) and an independent variable (i.e., a variable that may have its value freely chosen without considering the values of any other variables), wherein each input value for the independent variable relates to exactly one output value for the dependent variable. Conventional notation for an equation that relates a y-value (i.e., the dependent variable) "as a function of" an x-value (i.e., the independent variable) is $y=f(x)$.

As used herein, "optimizing" or "fitting" an equation refers to a process, as commonly practiced in mathematical modeling or curve fitting procedures, for obtaining numerical values for coefficients in an equation to yield an expression that "fits" or approximates experimental measurements. Typically, an optimized equation will define a best-fit curve.

As used herein, the terms "optimized equation," and "fitted equation" are alternative references to an equation containing fixed numerical values for coefficients as the result of an optimizing procedure. "Fitted" curves result from optimizing an equation.

By "local" is meant relating to an end-user. For example, a local instrument refers to an end-user's instrument. A local calibration plot refers to a calibration plot using results obtained by an end-user, for example by conducting an amplification reaction on the local instrument.

By "re-calibrate" or "re-calibration" is meant a calibration procedure or result subsequent to an earlier calibration procedure or result that is performed or obtained using the same instrument. For example, the first time a calibration procedure is performed using an instrument that amplifies nucleic acids and monitors amplicon synthesis as a function of cycle numbers or time (e.g., a real-time PCR instrument), two different calibration standards may be amplified and a calibration plot may result. The calibration plot may mathematically relate a ratio value as a function of the starting target amount input into the amplification reaction. A re-calibration procedure would employ that same instrument for producing a subsequent or updated calibration plot.

By "calibration plot" is meant a graphical or mathematical representation relating a quantity that can be measured for an amplification reaction (e.g., a ratio of measured threshold values for amplified target and internal calibrator) to a known amount of substrate input into the amplification reaction (e.g., the starting amount of target nucleic acid). A calibration plot preferably is established using computer spreadsheet software, and includes electronic representations of calibration results or information. "Calibration plot" and "calibration curve" are used interchangeably. It is to be understood that a calibration plot or curve can refer to linear and non-linear calibration curves.

As used herein, a "fixed-point" is a data point (e.g., having x- and y-coordinates) that can be used for establishing a calibration plot in a calibration or re-calibration procedure, where that data point does not change with time. The fixed-point may be determined and used on a single apparatus (e.g., a local instrument). Alternatively, the fixed-point may be determined using an apparatus at an assay kit manufacturer's site, and then used by a customer or end-user on a different apparatus.

By "kit" is meant a packaged combination of materials, typically intended for use in conjunction with each other. Kits in accordance with the disclosure may include instructions or other information in a "tangible" form (e.g., printed information, electronically recorded on a computer-readable medium, or otherwise recorded on a machine-readable medium such as a bar code for storing numerical values).

By "consisting essentially of" is meant that additional component(s), composition(s) or method step(s) that do not materially change the basic and novel characteristics of the present disclosure may be included in the present disclosure. Any component(s), composition(s), or method step(s) that have a material effect on the basic and novel characteristics of the present disclosure would fall outside of this term.

Preferred Nucleic Acid Amplification Methods

Examples of amplification methods useful in connection with the present disclosure include, but are not limited to: Transcription Mediated Amplification (TMA), Single-Primer Nucleic Acid Amplification, Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. patent application Ser. No. 11/213,519, published European patent application EP 0 525 882, U.S. Pat. No. 4,965,188, U.S. Pat. No. 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform nucleic acid amplification reactions are hereby incorporated by reference.

The disclosed algorithm and method also can be used for processing results obtained using amplification reactions that require only a single extendable primer. These reactions include transcription-associated amplification systems that employ a single extendable primer in combination with a 3'-blocked oligonucleotide that cannot be extended by a nucleic acid polymerase. Methods for carrying out such amplification reactions are, for example, detailed in U.S. patent application Ser. No. 11/213,519.

Examples of Useful Indicia of Amplification

A variety of indicia of amplification can be used in connection with the disclosed method. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720, the disclosure of which is incorporated by reference herein. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934, the disclosure of which is incorporated by reference. Still other useful indicia of amplification include "TTime" and "TArc." Notably, different approaches for determining TArc values employ directionally similar vectors (i.e., resulting in a value identified simply by "TArc"), and directionally opposed vectors (i.e., resulting in a value identified as "OTArc"). Still other techniques involve identifying cycle threshold (e.g., "Ct") values as the time or cycle number during a reaction at which a signal, preferably a fluorescent signal, equals a static threshold (e.g., a predetermined static threshold value). General descriptions of these methods latter are given below.

Methods of Determining TTime Values

Simply stated, TTime values estimate the time at which a particular threshold indicating amplicon production is passed in a real-time amplification reaction. The algorithm for calculating and using TTime values has been described in the U.S. patent application identified by Ser. No. 60/659,874, the disclosure of which is incorporated by reference. According to this algorithm, a curve fit procedure is applied to normalized and background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve which fits the data, is to estimate the time corresponding to the point at which the curve or a projection thereof intersects a predetermined static threshold value. In one embodiment, the threshold for normalized data is 0.11. The high and low bounds are determined empirically as that range over which curves fit to a variety of control data sets exhibit the least variability in the time associated with the given threshold value. In one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined.

Methods of Determining TArc Values

Time-dependent indicia of amplification referred to as "TArc" and "OTArc" are determined using vector-based analyses of real-time run curves. The TArc value identifies the point in time at which a growth curve begins to curve or "inflect" upward. This determined point can be used for creating a standard curve, or for establishing a parameter of an amplification reaction that relates to the amount or concentration of an analyte polynucleotide in a test sample. The vector analysis is most conveniently carried out using growth curves having data points distributed over substantially uniform time intervals. Detailed presentations concerning the determination and use of TArc and OTArc values appear in the U.S. Pat. No. 7,739,054, which is incorporated by reference herein.

Preferred Systems and Apparatus

The methods disclosed herein are conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of a product undergoing analysis. In a highly preferred embodiment, software for executing the calibration algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

Preferably, when the computer used for executing the disclosed calibration algorithm is an integral component of an apparatus for performing and analyzing real-time nucleic acid amplification reactions, the apparatus preferably comprises a temperature-controlled incubator, a detection device for collecting signals, an analyzing device (e.g., a computer or processor) for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the disclosed methods will be conventional components that will be familiar to those having an ordinary level of skill in the art. The temperature-controlled incubator used to perform and analyze real-time nucleic acid amplification may be of a conventional design which can hold a plurality of reaction tubes, or reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Computer Program Products

Included within the scope of the disclosure are software-based products (e.g., tangible embodiments of software for instructing a computer to execute various procedural steps) that can be used for performing the data processing method. These include software instructions stored on computer-readable media, such as magnetic media, optical media, "flash" memory devices, and computer networks. As well, the disclosure embraces a system or an apparatus that amplifies nucleic acids, detects nucleic acid amplification products, and processes results to indicate a quantitative result for target in a test sample. Although the various components of the apparatus preferably function in a cooperative fashion, there is no requirement for the components to be part of an integrated assembly (e.g., on a single chassis). However, in a preferred embodiment, components of the apparatus are connected together. Included within the meaning of "connected" are connections via wired and wireless connections.

Particularly falling within the scope of the disclosure is an apparatus or system that includes a computer linked to a device that amplifies nucleic acids and monitors amplicon synthesis as a function of cycle number or time, where the computer is programmed to execute the quantitative algorithm disclosed herein. An exemplary system in accordance with the disclosure will include a temperature-controlled incubator, and a fluorimeter cabable of monitoring and distinguishing at least two wavelengths of fluorescent emissions. These emissions may used to indicate target amplicon synthesis, and IC amplicon synthesis.

Single-Point Calibration and Re-Calibration Procedures Facilitate Random Access Format Modern "random-access" devices that quantify target nucleic acids in test samples using real-time amplification advantageously will permit an end user to cycle reagents on-and-off the instrument multiple times. Reagents for a single kit may, therefore, be loaded/unloaded several times before a kit is used completely. As a result, it may be necessary to re-run the calibration plot (e.g., each time the kit is loaded onto the instrument). Significant kit resources could be expended to accommodate the random-access feature if two or more calibrators were employed for each calibration or re-calibration procedure. However, this process can be simplified using a fixed-point approach, as disclosed herein.

In one preferred embodiment, the fixed-point is established by an assay manufacturer and then provided to a customer or end-user in connection with purchase of a kit. For example, a collection of calibration standards can be amplified on an instrument at the assay manufacturer's location, whereby indicia of amplification are determined for each of the analyte polynucleotide standard and the IC. Dividing these values, one by the other (e.g., $C_T$Target/$C_T$IC) establishes ratio values that may be plotted using electronic spreadsheet software. Fitting a curve or line to the collected points results in a first calibration plot. Extending the calibration plot to the point at which the ratio value equals zero identifies a point that can be used as a fixed-point. More particularly, the extrapolated point at which the input target amount or concentration would correspond to a ratio value of zero can be used as a fixed-point for preparing calibration plots on the same instrument, or even a different instrument. Stated differently, all calibration plots prepared using a single adjustment calibrator would share that same fixed-point.

In a different preferred embodiment, the fixed-point to be used for internal calibration adjustment may be prepared by the end-user using only the local instrument. For example, this can involve determining the input amount or concentration of analyte polynucleotide standard expected to yield a ratio value of zero. Of course, this will entail additional effort, at least initially, on the part of the end-user. Perhaps balancing this is the possible benefit of creating reference curves specific to a particular instrument.

In certain embodiments, a conventional calibration plot can be established by an end-user on a local instrument the first time a kit is used. This may involve performance of two calibration reactions. Time-dependence or cycle number dependence of amplification for target and IC in both calibrators can be determined and normalized, for example by dividing the indicia for target by the indicia for IC that amplified in the same reaction. The two points can be used to establish a calibration plot that can be used immediately for quantifying target nucleic acids in test samples. Separately, the resulting calibration plot can be projected to identify the point corresponding to the input target quantity or concentration associated with a ratio value of zero. This projected point can be used as the fixed-point for preparing re-calibration plots. Although not used for creating the initial calibration plot, the identified fixed-point can be stored for use in conjunction with re-calibration procedures.

System re-calibration can be carried out using as few as a single adjustment calibrator. Given availability of a fixed-point, indicia of amplification for target and coamplified IC can be normalized to give a ratio value, and the normalized result used in combination with the fixed-point to result in a complete calibration curve.

Generally speaking, there is a clear advantage to performing calibration and re-calibration procedures using minimal resources to facilitate periodic instrument calibration. Indeed, conserving laboratory resources is a reason for employing the single-point system calibration or re-calibration procedure.

Preferred Methods of Selecting Reference Calibration Curves and Fixed-Points

Fixed-points on calibration plots of the ratio of indicia of amplification for target and IC as a function of input target amount or concentration, as employed in the disclosed calibration approach, can be determined in a variety of ways. In certain preferred approaches, pooled results from amplification and detection of a plurality of calibration standards using different real-time amplification and detection instruments are combined, and a single best-fit calibration curve fitted to the pooled data (i.e., pooled indicia of amplification data points from each of the different calibration standards). This effectively averages-out variation in the calibration plot that results from conducting the assay on different instruments (e.g., belonging to the assay manufacturer and the end-user). In an alternative approach (demonstrated in the working Examples, herein), a single calibration curve was established using results from only a single real-time instrument. Generally speaking, once the calibration curve is established by some means, there follows a process of selecting a fixed-point to be used in combination with a result from a single adjustment calibrator run on the same or a different instrument. This may involve testing candidate points from the calibration curve (e.g., corresponding to the different calibration standards, interpolated data points, or extrapolated data points) in combination with results from the adjustment calibrator to yield an "adjusted" calibration curve useful for quantifying analyte polynucleotide under a variety of conditions. These different conditions may include running the assay on different instruments, or using aged or "stressed" reagent conditions, etc.

In other preferred approaches, the fixed-point is identified as the input target amount or concentration that, by extrapolation of a calibration plot would yield a ratio value (e.g., $C_T$Target/$C_T$IC or TTimeTarget/TTimeIC, etc.) of zero. In one preferred method, plots are generated using calibration data produced on one or more different instruments. For example, one or more instruments at an assay manufacturer's site may be used to determine the fixed-point which is then provided to an end-user of the kit for use on the end-user's instrument (i.e., an instrument different from the one(s) used for making the determination). Alternatively, the fixed-point can be determined on the same instrument that is used for quantifying target nucleic acid in samples undergoing testing (e.g., a local instrument). In this instance, the end user may carry out amplification reactions on a single instrument, use the resulting data to produce a plurality of calibration plots, and then use the calibration plots to determine the fixed-point. If more than two calibration plots are available, it may be desirable to determine the fixed-point by averaging input target values associated with ratio values of zero. In certain preferred embodiments, calibration plots used for establishing fixed-points are, themselves, prepared using a plurality of different calibration standards. In certain highly preferred embodiments, calibration plots used for establishing fixed-points are prepared using two different calibration standards.

Working Examples

Nucleic acid target capture and amplification procedures in all of the following Examples were performed at Gen-Probe Incorporated (San Diego, Calif.) using an automated instrument capable of amplifying nucleic acids under temperature-controlled conditions, and monitoring amplicon production (e.g., by optical monitoring of fluorescence) as a function of cycle number or time. Published U.S. Patent Application 2011/0147610, the entire disclosure of which is incorporated by reference herein, details features of a preferred instrument for performing real-time amplification procedures. Another preferred instrument is described in U.S. Pat. No. 6,713,297, the disclosure of which is incorporated by reference herein. Synthetic transcripts for analyte target and IC served as templates in the reactions. Samples to be processed and amplified were prepared by combining a constant 150,000 copies of synthetic IC transcript, and a 0.5 ml aliquot containing an amount of an analyte target transcript that served as a template for amplification. Concentration of the target nucleic acid used in the procedure ranged from $10^2$ to $10^7$ copies/ml across sets of six reactions. Amplification reactions were carried out using template nucleic acids following target-capture and wash steps to remove or reduce impurities in the samples. Target and IC templates were coamplified in the same reaction using independent primer sets (i.e., no shared primers). Amplification products were detected and monitored using distinguishably labeled, amplicon-specific molecular torch hybridization probes, each harboring a different fluorescent reporter. All amplification reactions were performed in replicates. Threshold time values representing indicia of amplification for each of the coamplified target and IC were determined using the TTime algorithm, essentially as described in published U.S. Patent Application No. 2006/0276972, the disclosure of which is incorporated by reference herein. Ratio values were calculated by dividing the TTime value determined for target (i.e., $TTime_{Target}$) by the TTime value determined for IC (i.e., $TTime_{IC}$) that amplified in the same reaction.

To be clear, the internal calibrator polynucleotide was the same in the calibration standards, in the adjustment calibrator, and in test sample amplification reactions. As well, the amount (e.g., starting concentration) of internal calibrator polynucleotide was the same in all reactions.

Example 1 describes how a linear reference calibration plot generated using a first instrument that amplifies nucleic acid and monitors amplicon production in a real-time format was used to establish a fixed-point for subsequent use in single-point calibration procedures. The first instrument is referred to below as instrument "V35."

Example 1

Establishing a Fixed-Point for Internal Calibration Adjustment

Six nucleic acid calibration standards were amplified in replicates of five using a first real-time instrument identified as V35. All reactions on instrument V35 were carried out using a standard target capture reagent ("TCR") for enriching target nucleic acid prior to amplification. Samples used for calibration reactions had volumes of 0.5 ml each, and nucleic acid target concentrations that ranged from $10^2$ to $10^7$ copies/ml. Nucleic acids captured from the different samples were co-amplified with a fixed 150,000 copies of IC in replicates. Measured TTime indicia of amplification for target and IC were normalized to yield threshold ratio values (i.e., $TTime_{Target}/TTime_{IC}$). A linear calibration plot of the ratio values as a function of input target quantity (e.g., concentration) was established and used for assigning actual target starting quantities, referred to herein as "value-assigned" quantities, to each different calibration standard. Table 1 presents summarized results and value-assigned concentrations of the calibration standards, where value-assignments were established using all six calibrators. Numerical results in Table 1 are presented using more than the appropriate two decimal places.

TABLE 1

Summarized Results for Calibration Standards Amplified on Instrument V35

| Cal. No. | Approximate Target Quantity (log copies/ml) | Value-Assigned Target Quantity (log copies/ml) | Ratio ($TTime_{Target}/TTime_{IC}$) |
|---|---|---|---|
| 1 | 2 | 2.0491 | 1.0582 |
| 2 | 3 | 2.9624 | 0.9424 |
| 3 | 4 | 3.9637 | 0.8155 |
| 4 | 5 | 4.9962 | 0.6847 |
| 5 | 6 | 6.0212 | 0.5548 |
| 6 | 7 | 7.0073 | 0.4298 |

The fitted linear calibration plot established using the data from instrument V35 (e.g., representing a first calibration reference curve) was defined by Equation 1, wherein X and Y are the target quantity (e.g., concentration) and ratio values, respectively.
Y = −0.1267 X + 1.3179 [Equation 1]
The X-intercept (i.e., the point at which the ratio value equals zero) calculated using Equation 1 was 10.3989. Thus, the fixed-point established by this procedure was (10.3989, 0).

Example 2 illustrates how the fixed-point established on the first real-time instrument (i.e., V35) could be used for processing results obtained on a second real-time instrument (i.e., referred to below as "V53"). Results obtained using instrument V53 for amplifying different calibration standards were individually paired with the fixed-point that had been established using instrument V35 to create linear calibration plots. These calibration plots were subsequently used for back-testing results from the remaining reactions carried out on instrument V53. Stated differently, one calibration standard was treated as an adjustment calibrator while other calibration standards were treated as mock test samples, and the quantities of target nucleic acid present in the mock test samples determined using the adjusted calibration curve determined using results from the adjustment calibrator and the fixed-point.

Example 2

Preparation of an Adjusted Calibration Curve that Incorporates the Fixed-Point

Nucleic acid amplification reactions similar to those described in Example 1 were performed and monitored using real-time instrument V53. Table 2 presents summarized results and value-assigned concentrations of the calibration standards, where value-assignments were made using all six calibrators. Value-assigned quantities are generally regarded as true quantitative values. Numerical results in Table 2 are presented using more than the appropriate two decimal places.

TABLE 2

Summarized Results for Calibration Standards Amplified on Instrument V53

| Cal. No. | Approximate Target Quantity (log copies/ml) | Value-Assigned Target Quantity (log copies/ml) | Ratio ($TTime_{Target}/TTime_{IC}$) |
|---|---|---|---|
| 1 | 2 | 2.0252 | 1.0421 |
| 2 | 3 | 3.0338 | 0.9174 |
| 3 | 4 | 3.9105 | 0.8090 |
| 4 | 5 | 4.9968 | 0.6746 |
| 5 | 6 | 6.0139 | 0.5488 |
| 6 | 7 | 7.0198 | 0.4244 |

Table 3 illustrates how a fixed-point established with a first instrument (V35) could be used in combination with a single result generated on a second instrument (V53) to produce an adjusted calibration curve. Ratio and value-assignment results from individual calibration standards 1-6 in Table 2 were paired with the fixed-point (10.3989, 0) to produce six different adjusted, linear calibration curves. For example, the first linear calibration plot was based on the two points (2.0252, 1.0424) and (10.3989, 0). In this manner, each calibration standard was independently treated as a mock adjustment calibration standard. Remaining entries in Table 2 that were not used to establish the adjusted linear calibration curves then served as mock test samples, and target amounts were calculated. Differences between the value-assigned target quantities and the values calculated using the adjusted calibration curves also are presented in Table 3. All tabulated values are in log copies/ml.

TABLE 3

Single-Point Calibration Using One Fixed-Point and Results from One Adjustment Calibrator

| Cal. No. | Cal. No. 1 | | Cal. No. 2 | | Cal. No. 3 | | Cal. No. 4 | | Cal. No. 5 | | Cal. No. 6 | |
|---|---|---|---|---|---|---|---|---|---|---|---|---|
| | Calc. Target | Difference | Calc. Target | Difference | Calc. Target | Difference | Calc. Target | Difference | Calc. Target | Difference | Calc. Target | Difference |
| 1 | N/A | N/A | 2.03 | 0.01 | 2.04 | 0.02 | 2.05 | 0.03 | 2.07 | 0.05 | 2.10 | 0.08 |
| 2 | 3.03 | −0.01 | N/A | N/A | 3.04 | 0.01 | 3.05 | 0.02 | 3.07 | 0.03 | 3.09 | 0.06 |
| 3 | 3.90 | −0.01 | 3.90 | −0.01 | N/A | N/A | 3.92 | 0.01 | 3.93 | 0.02 | 3.96 | 0.05 |
| 4 | 4.98 | −0.02 | 4.98 | −0.01 | 4.99 | −0.01 | N/A | N/A | 5.01 | 0.01 | 5.03 | 0.03 |
| 5 | 5.99 | −0.02 | 5.99 | −0.02 | 6.00 | −0.02 | 6.00 | −0.01 | N/A | N/A | 6.03 | 0.02 |
| 6 | 6.99 | −0.03 | 6.99 | −0.03 | 7.00 | −0.02 | 7.00 | −0.02 | 7.01 | −0.01 | N/A | N/A |

All numerical values in log copies/ml
N/A = not applicable

Example 3 illustrates how the fixed-point established by the method described above also could be used in a procedure for quantifying the nucleic acid target using reagents compromised by accelerated degradation.

Example 3

Quantifying Target Nucleic Acids Using Reagents Subjected to Accelerated Degradation Conditions

Six nucleic acid calibration standards were amplified using a third real-time instrument identified as V47. All reactions were carried out using a TCR that had been subjected to heating at 55° C. for 28 days to promote accelerated degradation. All other amplification reaction and monitoring conditions were similar to those described above.

Table 4 presents summarized results and value-assigned concentrations of the calibration standards, where value-assignments were made using all six calibrators. Numerical results in Table 4 are presented using more than the appropriate two decimal places.

TABLE 4

Summarized Results for Calibration Standards Amplified on Instrument V47 Using Reagents Subjected to Accelerated Degradation

| Cal. No. | Approximate Target Quantity (log copies/ml) | Value-Assigned Target Quantity (log copies/ml) | Ratio ($TTime_{Target}/TTime_{IC}$) |
|---|---|---|---|
| 1 | 2 | 2.1562 | 0.8380 |
| 2 | 3 | 2.8550 | 0.7628 |
| 3 | 4 | 3.9198 | 0.6482 |
| 4 | 5 | 4.9764 | 0.5344 |
| 5 | 6 | 6.0870 | 0.4148 |
| 6 | 7 | 7.0057 | 0.3159 |

As above, results from individual calibration standards 1-6 in Table 4 were paired with the fixed-point (10.3989, 0) established using instrument V35 to produce six different adjusted, linear calibration curves. In this manner, each calibration standard was independently treated as a mock adjustment calibration standard. Remaining entries in Table 4 that were not used to establish the adjusted linear calibration curves then served as mock test samples, and target amounts were calculated. Differences between the value-assigned target quantities and the values calculated using the adjusted calibration curves also are presented in Table 5. All tabulated values are in log copies/ml.

TABLE 5

Single-Point Calibration Using One Fixed-Point and Results Obtained Using Aged Reagents

| | Cal. No. 1 | | Cal. No. 2 | | Cal. No. 3 | | Cal. No. 4 | | Cal. No. 5 | | Cal. No. 6 | |
|---|---|---|---|---|---|---|---|---|---|---|---|---|
| Cal. No. | Calc. Target | Difference | Calc. Target | Difference | Calc. Target | Difference | Calc. Target | Difference | Calc. Target | Difference | Calc. Target | Difference |
| 1 | N/A | N/A | 2.11 | −0.04 | 2.02 | −0.13 | 1.90 | −0.26 | 1.69 | −0.47 | 1.40 | −0.76 |
| 2 | 2.90 | 0.04 | N/A | N/A | 2.77 | −0.08 | 2.66 | −0.20 | 2.47 | −0.39 | 2.21 | −0.65 |
| 3 | 4.02 | 0.10 | 3.99 | 0.07 | N/A | N/A | 3.82 | −0.10 | 3.66 | −0.26 | 3.44 | −0.48 |
| 4 | 5.14 | 0.17 | 5.11 | 0.14 | 5.06 | 0.08 | N/A | N/A | 4.84 | −0.13 | 4.66 | −0.32 |
| 5 | 6.32 | 0.23 | 6.30 | 0.21 | 6.25 | 0.17 | 6.19 | 0.10 | N/A | N/A | 5.94 | −0.14 |
| 6 | 7.29 | 0.29 | 7.27 | 0.27 | 7.24 | 0.24 | 7.19 | 0.19 | 7.12 | 0.11 | N/A | N/A |

All numerical values in log copies/ml
N/A = not applicable

Example 4 illustrates advantages of the disclosed single point calibration approach by processing the data from Tables 2 and 4 using a different fixed-point. More particularly, rather than using the fixed point established in Example 1, a different point on the calibration curve produced using instrument V35 was established. As indicated below, this different fixed-point yielded very good results when processing data obtained using standard reagents, but performed poorly when processing data obtained using reagents that had been subjected to accelerated degradation conditions.

Example 4

Use of a Different Fixed-Point Leads to Differential Quantitative Ability

Equation 1 was solved to determine the coordinates of a point on the linear calibration curve produced using instrument V35, where the point corresponded to an input target level of 7 log copies/ml of the analyte polynucleotide standard. This point had the coordinates (7, 0.431).

Results from individual calibration standards 1-6 in Table 2 were paired with the fixed-point (7, 0.431) to produce six different adjusted, linear calibration curves. In this manner, each calibration standard was independently treated as a mock adjustment calibration standard. Remaining entries in Table 2 that were not used to establish the adjusted linear calibration curves then served as mock test samples, and target amounts were calculated. Differences between the value-assigned target quantities (i.e., representing gold standard values) and the values determined using the adjusted calibration curves also are presented in Table 6. All tabulated values are in log copies/ml.

TABLE 6

Single-Point Calibration Using One Fixed-Point and Results Obtained Using Standard Reagents

| Cal. No. | Cal. No. 1 | | Cal. No. 2 | | Cal. No. 3 | | Cal. No. 4 | | Cal. No. 5 | |
|---|---|---|---|---|---|---|---|---|---|---|
| | Calc. Target | Difference | Calc. Target | Difference | Calc. Target | Difference | Calc. Target | Difference | Calc. Target | Difference |
| 1 | N/A | N/A | 2.02 | −0.01 | 2.01 | −0.02 | 1.97 | −0.05 | 1.88 | −0.14 |
| 2 | 3.04 | 0.01 | N/A | N/A | 3.02 | −0.01 | 3.00 | −0.03 | 2.93 | −0.11 |
| 3 | 3.92 | 0.01 | 3.92 | 0.01 | N/A | N/A | 3.89 | −0.02 | 3.84 | −0.07 |
| 4 | 5.02 | 0.02 | 5.01 | 0.02 | 5.01 | 0.01 | N/A | N/A | 4.96 | −0.04 |
| 5 | 6.04 | 0.03 | 6.04 | 0.03 | 6.04 | 0.02 | 6.03 | 0.02 | N/A | N/A |
| 6 | 7.05 | 0.03 | 7.05 | 0.03 | 7.05 | 0.03 | 7.05 | 0.03 | 7.06 | 0.04 |

All numerical values in log copies/ml
N/A = not applicable

Results from individual calibration standards 1-6 in Table 4 were paired with the fixed-point (7, 0.431) to produce six different adjusted, linear calibration curves. In this manner, each calibration standard was independently treated as a mock adjustment calibration standard. Remaining entries in Table 4 that were not used to establish the adjusted linear calibration curves then served as mock test samples, and target amounts were calculated. Differences between the value-assigned target quantities and the values calculated using the adjusted calibration curves also are presented in Table 7. All tabulated values are in log copies/ml.

TABLE 7

Single-Point Calibration Using One Fixed-Point and Results Obtained Using Reagents Subjected to Accelerated Degradation

| Cal. No. | Cal. No. 1 | | Cal. No. 2 | | Cal. No. 3 | | Cal. No. 4 | | Cal. No. 5 | |
|---|---|---|---|---|---|---|---|---|---|---|
| | Calc. Target | Difference | Calc. Target | Difference | Calc. Target | Difference | Calc. Target | Difference | Calc. Target | Difference |
| 1 | N/A | N/A | 1.92 | −0.24 | 1.23 | −0.93 | −0.97 | −3.12 | 29.94 | 27.78 |
| 2 | 3.05 | 0.20 | N/A | N/A | 2.29 | −0.56 | 0.51 | −2.35 | 25.7 | 22.84 |
| 3 | 4.42 | 0.50 | 4.29 | 0.37 | N/A | N/A | 2.75 | −1.17 | 19.24 | 15.32 |
| 4 | 5.77 | 0.79 | 5.71 | 0.73 | 5.53 | 0.56 | N/A | N/A | 12.83 | 7.85 |
| 5 | 7.19 | 1.11 | 7.20 | 1.12 | 7.23 | 1.14 | 7.32 | 1.23 | N/A | N/A |
| 6 | 8.37 | 1.36 | 8.44 | 1.43 | 8.63 | 1.63 | 9.25 | 2.25 | 0.51 | −6.49 |

All numerical values in log copies/ml
N/A = not applicable

The foregoing illustrates how different points from a single calibration curve (e.g., a "first" calibration curve) can be evaluated as candidate fixed points for use in combination with a result from a single adjustment calibrator to reproduce a complete calibration curve (i.e., the adjusted calibration curve). Clearly there are differences between the value of the resulting adjusted calibration curves with respect to quantifying analyte polynucleotide in test samples. While the x-intercept and one point from the first calibration curve were used to illustrate the technique, it is to be understood that any number of points from along the first calibration curve can be chosen for analysis. For example, additional points from the first calibration curve that could be tested include, without limitation: the y-intercept, the x-intercept, values corresponding to input amounts of analyte polynucleotide used in the various calibration standards, or even points interpolated between calibration standard data points, or extrapolated beyond the dynamic range of the assay.

The process for selecting which point should be used as a fixed point, for processing quantitative results obtained using a local instrument that generates a growth curve, may take account of different considerations. These considerations include, again without limitation: reagent stability, cycling reagents between different temperatures, the use of different temperature conditions for performing nucleic acid amplification, etc. It may be desirable to assess precision in recovered concentration of calibration standards, and to select the fixed point based on the highest precision delivered thereby.

This disclosure has been described with reference to a number of specific examples and embodiments thereof. Of course, a number of different embodiments of the present disclosure will suggest themselves to those having ordinary skill in the art upon review of the foregoing detailed description. Thus, the true scope of the present disclosure is to be determined upon reference to the appended claims.

What is claimed is:

1. A method of quantifying an analyte polynucleotide in a sample with an adjusted calibration curve using a local instrument, said method comprising the steps of:
   (a) obtaining a pair of coordinates for a fixed-point on a calibration curve specific for a quantitative assay, wherein the pair of coordinates specify an amount of an analyte polynucleotide and a normalized indicia of amplification value, and wherein the fixed-point was not determined using the local instrument, or was previously determined and stored for later use;
   (b) obtaining an adjustment calibrator that comprises a fixed amount of an internal calibrator and a known amount of the analyte polynucleotide;
   (c) co-amplifying the analyte polynucleotide and the internal calibrator of the adjustment calibrator using the local instrument, wherein the local instrument comprises a memory, and amplifies nucleic acid and monitors amplicon synthesis as amplification is occurring, and wherein the fixed-point is stored in the memory of the local instrument;

(d) determining indicia of amplification for each of the analyte polynucleotide and the internal calibrator that co-amplified in step (c) using the local instrument;

(e) normalizing the indicia of amplification determined for the analyte polynucleotide to the indicia of amplification determined for the internal calibrator using the local instrument;

(f) establishing the adjusted calibration curve by preparing a calibration plot that comprises a first point and a second point using the local instrument, wherein the first point comprises coordinates for the known amount of the analyte polynucleotide of the adjustment calibrator and the normalized indicia of amplification for the analyte polynucleotide determined in step (d), wherein the second point comprises the pair of coordinates, obtained in step (a), for the fixed-point, and wherein the adjusted calibration curve is stored in the memory of the instrument;

(g) amplifying the analyte polynucleotide of the sample using the local instrument;

(h) determining indicia of amplification for the analyte polynucleotide amplified in step (g) using the local instrument; and (i) determining the quantity of the analyte polynucleotide in the sample from the adjusted calibration curve and the indicia of amplification of the analyte polynucleotide using the local instrument.

2. The method of claim 1, wherein the amount of the analyte polynucleotide specified by the pair of coordinates obtained in step (a) is determined using a first real-time amplification and monitoring instrument other than the local instrument, and is not determined using results from any amplification reaction performed with the local instrument.

3. The method of claim 2, further comprising the step of co-amplifying with the first real-time instrument the analyte polynucleotide and the internal calibrator contained in each of a plurality of calibration standards, wherein each of the plurality of calibration standards comprises a different starting concentration of the analyte polynucleotide of the adjustment calibrator, and wherein the concentrations of the internal calibrator in each of the plurality of calibration standards and in the adjustment calibrator are substantially identical.

4. The method of claim 2, wherein the calibration curve of step (a) and the adjusted calibration curve established in step (f) are both linear calibration curves described by linear equations.

5. The method of claim 2, wherein step (a) and step (b) collectively comprise obtaining a kit that comprises the adjustment calibrator and a tangible embodiment of the pair of coordinates for the fixed-point.

6. The method of claim 5, wherein the tangible embodiment comprises a machine-readable barcode.

7. The method of claim 1, wherein before step (a) there is the step of preparing the calibration curve specific for the quantitative assay by fitting an equation to a collection of results obtained using a plurality of instruments, other than the local instrument, that amplify nucleic acid and monitor amplicon synthesis as amplification is occurring, and wherein the collection of results does not comprise results obtained using the local instrument.

8. The method of claim 1, wherein, step (f) comprises establishing the adjusted calibration curve by preparing, with a processor in communication with the local instrument, the calibration plot that comprises the first point and the second point.

9. The method of claim 8, wherein the processor in communication with the local instrument is an integral component of the local instrument.

10. The method of claim 1, wherein the pair of coordinates obtained in step (a) specifies the amount of the analyte polynucleotide when the normalized indicia of amplification value of the calibration curve is zero.

11. The method of claim 2, wherein the pair of coordinates obtained in step (a) specifies the amount of the analyte polynucleotide when the normalized indicia of amplification value of the calibration curve is zero.

12. The method of claim 7, wherein the pair of coordinates obtained in step (a) specifies the amount of the analyte polynucleotide when the normalized indicia of amplification value of the calibration curve is zero.

13. The method of claim 1, wherein obtaining step (b) comprises combining the fixed amount of the internal calibrator and the known amount of the analyte polynucleotide.

14. A computer program product for quantifying an analyte polynucleotide that may be present in a test sample using a nucleic acid amplification assay that comprises co-amplification of the analyte polynucleotide and a fixed amount of an internal calibrator, said computer program product comprising a non-transitory tangible embodiment of software instructions, wherein the computer program product is configured to run on a processor in communication with a memory and a local instrument that amplifies nucleic acids and monitors amplicon synthesis as a function of time, and the software instructions are for performing the steps of:

(a) receiving a pair of coordinates for a previously determined fixed-point on a calibration curve specific for the nucleic acid amplification assay to be used for quantifying the analyte polynucleotide, wherein the pair of coordinates specify an amount of the analyte polynucleotide and a normalized indicia of amplification value;

(b) obtaining a value for indicia of amplification for a known amount of the analyte polynucleotide normalized to indicia of amplification for the fixed amount of the internal calibrator contained in an adjustment calibrator and that co-amplified in a first amplification reaction performed with the local instrument;

(c) preparing an adjusted calibration curve that comprises a first point and a second point and storing the adjusted calibration curve in the memory, wherein the first point comprises coordinates for the known amount of the analyte polynucleotide of the adjustment calibrator and the value obtained in step (b), and wherein the second point comprises the pair of coordinates, received in step (a), for the fixed-point;

(d) obtaining a value for indicia of amplification for an unknown amount of the analyte polynucleotide in the test sample normalized to indicia of amplification for the fixed amount of the internal calibrator that co-amplified therewith in a second amplification reaction performed with the local instrument;

(e) comparing the value obtained in step (d) with the adjusted calibration curve to yield a quantitative result for the unknown amount of the analyte polynucleotide present in the test sample; and (f) outputting a tangible record of the quantitative result from step (e).

15. The computer program product of claim 14, wherein the pair of coordinates received in step (a) specifies the amount of the analyte polynucleotide when the calibration curve is projected to a normalized indicia of amplification value of zero.

16. The computer program product of claim 14, wherein the tangible embodiment of software instructions comprises software instructions stored on a medium selected from the group consisting of: an optical disk, a magnetic storage medium, a flash drive, a computer hard drive, and a network drive accessible by at least one computer.

17. The computer program product of claim 14, wherein step (b) and step (d) each comprise obtaining by mathematically calculating.

18. The computer program product of claim 14, wherein steps (b) and (d) comprise obtaining by receiving numerical inputs for the respective values.

19. The computer program product of claim 14, wherein the adjusted calibration curve prepared in step (c) is defined by a linear equation.

20. The computer program product of claim 14, wherein the tangible record of step (e) is printed on paper.

21. The computer program product of claim 14, wherein the nucleic acid amplification assay is an isothermal nucleic acid amplification assay.

22. An apparatus for determining the starting quantity of a target nucleic acid sequence in a test sample, the apparatus comprising:
   (a) at least one detection mechanism configured to measure:
      (i) signals indicative of the respective quantities of the target nucleic acid sequence and of a first internal calibrator being amplified in a first nucleic acid amplification reaction,
      wherein the first internal calibrator comprises a second nucleic acid sequence different from the target nucleic acid sequence;
      (ii) signals indicative of the respective quantities of a known amount of an analyte polynucleotide and a second internal calibrator being amplified in a second nucleic acid amplification reaction,
      wherein the analyte polynucleotide and the second internal calibrator are both components of an adjustment calibrator,
      wherein the second internal calibrator comprises the second nucleic acid sequence, and
      wherein the starting quantity of the second nucleic acid sequence is substantially equal in the first and second nucleic acid amplification reactions;
   (b) at least one processor in communication with the detection mechanism,
      wherein the processor is programmed with a pair of coordinates for a fixed-point specifying an analyte polynucleotide amount and a normalized indicia of amplification value, wherein the fixed-point was previously determined and stored for later use or was not determined using the apparatus, and
      wherein the processor further is programmed to perform the steps of:
         (i) obtaining from the measured signals a value for indicia of amplification for the known amount of the analyte polynucleotide normalized to indicia of amplification for the fixed amount of the internal calibrator contained in the adjustment calibrator co-amplified in the second nucleic acid amplification reaction;
         (ii) preparing an adjusted calibration curve that comprises a first point and a second point and storing the adjusted calibration curve in a memory in communication with the processor,
         wherein the first point comprises coordinates for the known amount of the analyte polynucleotide of the adjustment calibrator and the value obtained in step (i), and
         wherein the second point comprises the pair of coordinates for the fixed-point with which the processor is programmed;
         (iii) obtaining from the measured signals a value for indicia of amplification for the amount of the target polynucleotide in the test sample normalized to indicia of amplification for the fixed amount of the internal calibrator co-amplified therewith in the first nucleic acid amplification reaction;
         (iv) comparing the value obtained in step (iii) with the adjusted calibration curve to yield a quantitative result for the unknown amount of the analyte polynucleotide present in the test sample; and
         (v) outputting a tangible record of the quantitative result from step (iv).

23. The apparatus of claim 22, wherein the pair of coordinates for the fixed-point are determined using results from a plurality of nucleic acid amplification reactions performed using only an apparatus other than the apparatus that performed the first and second nucleic acid amplification reactions.

24. The apparatus of claim 23, wherein one member of said pair of coordinates specifies a normalized indicia of amplification value of zero.

25. The apparatus of claim 23, further comprising a temperature-controlled incubator in which the first and second nucleic acid amplification reactions take place.

26. The apparatus of claim 25, wherein the temperature-controlled incubator maintains a substantially constant temperature, and wherein the first and second nucleic acid amplification reactions are isothermal nucleic acid amplification reactions.

27. The apparatus of claim 23, wherein the adjusted calibration curve in step (ii) is defined by a linear equation.

28. The apparatus of claim 23, wherein said at least one detection mechanism comprises a fluorometer that measures fluorescent signals.

29. A method of quantifying an analyte polynucleotide in a sample with an adjusted calibration curve for a quantitative assay performed using a local instrument, said method comprising the steps of:
   (a) obtaining a pair of coordinates for a fixed-point on a calibration curve specific for the quantitative assay,
      wherein the pair of coordinates specify an amount of an analyte polynucleotide and an indicia of amplification value, and wherein the fixed-point was not determined using the local instrument, or was previously determined and stored for later use;
   (b) obtaining an analyte polynucleotide standard that comprises a known amount of the analyte polynucleotide;
   (c) amplifying the analyte polynucleotide of the analyte polynucleotide standard in a nucleic acid amplification reaction using the local instrument, wherein the local instrument comprises a memory, and amplifies nucleic acid and monitors amplicon synthesis as amplification is occurring, and wherein the fixed-point is stored in the memory of the local instrument;

(d) determining indicia of amplification for the analyte polynucleotide that amplified in step (c) using the local instrument; and (e) establishing the adjusted calibration curve by preparing a calibration plot that comprises a first point and a second point using the local instrument, wherein the first point comprises coordinates for the known amount of the analyte polynucleotide of the analyte polynucleotide standard and indicia of amplification determined in step (d), wherein the second point comprises the pair of coordinates, obtained in step (a), for the fixed-point, and wherein the adjusted calibration curve is stored in the memory of the instrument;

(f) amplifying the analyte polynucleotide of the sample using the local instrument;

(g) determining indicia of amplification for the analyte polynucleotide amplified in step (f) using the local instrument; and (i) determining the quantity of the analyte polynucleotide in the sample from the adjusted calibration curve and the indicia of amplification of the analyte polynucleotide using the local instrument.

30. The method of claim 29,
wherein before step (a) there is the step of preparing the calibration curve specific for the quantitative assay by fitting an equation to a collection of results obtained using a plurality of instruments, other than the local instrument, that amplify nucleic acid and monitor amplicon synthesis as amplification is occurring, and wherein the collection of results does not comprise results obtained using the local instrument.

31. The method of claim 29, wherein step (e) comprises using a processor in communication with the local instrument to prepare the calibration plot.

* * * * *

UNITED STATES PATENT AND TRADEMARK OFFICE
CERTIFICATE OF CORRECTION

PATENT NO. : 9,976,175 B2
APPLICATION NO. : 14/211565
DATED : May 22, 2018
INVENTOR(S) : Sangeetha Vijaysri Nair, Xianqun Wang and Susan K. Yamagata Page 1 of 1

It is certified that error appears in the above-identified patent and that said Letters Patent is hereby corrected as shown below:

Column 28, Claim 27, Line 45, "(ii)" should read --(b)(ii)--.

Signed and Sealed this
Seventeenth Day of July, 2018

Andrei Iancu
*Director of the United States Patent and Trademark Office*